United States Patent
Kreh et al.

(10) Patent No.: US 7,292,328 B2
(45) Date of Patent: Nov. 6, 2007

(54) METHOD FOR INSPECTION OF A WAFER

(75) Inventors: Albert Kreh, Solms (DE); Henning Backhauss, Wetzlar (DE); Detlef Michelsson, Wetzlar-Naunheim (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 373 days.

(21) Appl. No.: 11/011,059

(22) Filed: Dec. 15, 2004

(65) Prior Publication Data

US 2005/0134839 A1   Jun. 23, 2005

(30) Foreign Application Priority Data

Dec. 19, 2003   (DE) ................ 103 59 722

(51) Int. Cl.
*G01N 21/00* (2006.01)
(52) U.S. Cl. ................ 356/237.2; 356/237.4
(58) Field of Classification Search ...... None
See application file for complete search history.

(56) References Cited

U.S. PATENT DOCUMENTS 6,437,862 B1 * 8/2002 Miyazaki et al. ........ 356/237.2
6,928,185 B2 * 8/2005 Yonezawa ............... 382/149

FOREIGN PATENT DOCUMENTS

DE   43 10 149 C2   5/1996
EP   0 455 857 A1   11/1991

OTHER PUBLICATIONS

Ingrid Peterson et al., "Lithography Defects: Reducing and Managing Yield Killers Through Photo Cell Monitoring", Yield Management Solutions, Spring 2000, pp. 17-24.

* cited by examiner

*Primary Examiner*—Michael P. Stafira
(74) *Attorney, Agent, or Firm*—Foley & Lardner LLP

(57) ABSTRACT

Defects on a wafer (26) can be detected using bright-field and/or dark-field illumination. The radiation incident onto the wafer (26) has, in this context, a substantial influence on the reliability of the measurement results. To improve the reliability of the measurement results, the wafer (26) is illuminated with an illumination device (12), adjustment of the illumination device (12), in particular its brightness and frequency, being accomplished in consideration of read-out stored illumination setpoints. These illumination setpoints are determined by way of a previous reference measurement.

18 Claims, 3 Drawing Sheets

METHOD FOR INSPECTION OF A WAFER

CROSS REFERENCE TO RELATED APPLICATIONS

This application claims priority of the German patent application 103 59 722.0 which is incorporated by reference herein.

FIELD OF THE INVENTION

The invention concerns a method for inspection of a wafer with an illumination device that emits an illuminating light beam that is incident onto a surface of the wafer, and with an image acquisition device for acquiring an image of the surface.

BACKGROUND OF THE INVENTION

In semiconductor production, wafers are sequentially processed in a plurality of process steps during the production process, a plurality of identical repeating pattern elements being produced on one wafer. With increasing integration density, demands in terms of the quality of the features configured on the wafers are rising. To allow the quality of the configured features to be checked, and any defects to be found, requirements in terms of the quality, accuracy, and reproducibility of the components and process steps that handle the wafer are correspondingly high. This means that in the production of a wafer, with the many process steps and many layers of photoresist or the like to be applied, reliable and timely detection of defects in the individual features is particularly important.

A device for handling disk-shaped objects in a treatment plane of a local clean room is known, for example, from DE 43 10 149 C2. Here magazine receptacles are provided that are adjustable in elevation with respect to the treatment plane. Workstations for processing or inspection purposes are located in the treatment plane. The treatment plane is arranged above an intermediate floor that subdivides the clean room into two sub-spaces one above another, in which an air stream component of an air stream is directed out of the sub-space above the intermediate floor into the sub-room, containing the drive parts, below the intermediate floor. The air flow prevents any abraded material caused by the drive elements from traveling to the workstations in the treatment plane. The air preparation system comprises a housing, and its air outlet is constituted by a circle-sector-shaped cutout having air-directing panels.

It is advantageous, after each process step is performed, to check the quality achieved with that step. After lithography, for example, during the manufacturing process and even before any subsequent process step, the quality achieved in each case can be reliably evaluated. Thus, if a determination is made, just after a process step is performed and even before a production process has been completed, that a wafer or features configured on the wafer are defective, the wafer can be immediately discarded with no need to perform additional subsequent process steps. Or wafers found to be defective can be reprocessed separately until satisfactory quality is achieved. Efficiency and yield in semiconductor production can thereby be enhanced.

Optical apparatuses are particularly suitable for inspecting the surface of wafers. Examination of the surface can be accomplished, for example, as is known from EP 455 857, by evaluating beams that are retroreflected from the surface of the wafer.

Also known are optical apparatuses that, by image recognition, can recognize a wide variety of features on the surface of a wafer. The wafer is usually illuminated in bright-field fashion in this context, and scanned with a camera (matrix or linear camera).

One such inspection apparatus of KLA-Tencor Corporation is described in the article "Lithography Defects: Reducing and Managing Yield Killers Through Photo Cell Monitoring," by Ingrid Peterson, Gay Thompson, Tony DiBiase, and Scott Ashkenaz, Spring 2000, Yield Management Solutions. The wafer inspection apparatus described therein operates with an incident-light illumination device that examines low-contrast microdefects using bright-field/dark-field illumination.

Defects on the wafer can be detected using bright-field and/or dark-field illumination, the radiation reflected respectively in diffuse or directional fashion from the wafer being evaluated. The radiation incident onto the wafer has a substantial influence on the reliability of the measurement result. If the illumination conditions change over time due a change in the adjustment of the lamp or because of aging effects in the illumination source, this can result in distorted or incorrect measurement results. In particular, defects can be simulated.

SUMMARY OF THE INVENTION

It is therefore the object of the present invention to propose a method for inspection of a wafer in which the reliability of the measurement result is enhanced.

This object is achieved, according to the present invention, by way of a method for inspection of a wafer comprising the steps of:
  emitting an illuminating light from an illumination device, wherein the light beam is incident onto a surface of the wafer,
  acquiring an image of the surface with an image acquisition device, and
  adjusting the illumination device, in particular adjustment of the brightness or frequency, wherein the adjusting is accomplished in consideration of read-in stored illumination setpoints.

Many features on the surface of wafers, for example conductor paths, etched depressions, or protrusions, proceed in substantially linear fashion. Defects in these features that accumulate along the linear features as a result of process step errors, or extend along the features or perpendicular to them, can be detected with particularly high contrast if the light used to illuminate the surface of the wafer is incident perpendicular to the features. There are, however, effects that distort the result of the detected features, or simulate an effect that is not present. These effects can derive, for example, from the status of the illumination source. To exclude or at least to reduce such effects, according to the present invention the illumination device that generates the illuminating light beam for illuminating the surface of the wafer is activated in such a way that the illumination is defined. In particular, activation is accomplished in such a way that an aging or other change in the emission characteristics of the radiation source or of the image acquisition device is compensated for. For that purpose, adjustment of the illumination device, in particular the adjustment of its brightness and frequency, is accomplished in consideration of read-out stored illumination setpoints.

These illumination setpoints are determined in a previous working step and stored. A reference field can be evaluated for the determination. In this evaluation, a reference field is illuminated by the illuminating light beam, and the image of the reference field is evaluated. This evaluation is accomplished, for example, with the aid of an image acquisition device such as, for example, a camera. Suitable activation values for the illumination device can be stored as the results of the evaluation, those values being usable for activation. Especially suitable for this purpose are the brightness, color-balance, voltage, and/or electrical current values determined from the measurement.

To allow the determination and adjustment of the illumination source to be integrated as optimally as possible into the wafer production process, it is useful to use a reference field that is easily and reproducibly available during production. For that purpose, the reference field can be embodied as a defined mirror surface, i.e. as a surface having defined reflectivity; as a grating; or as a two- or three-dimensional structure that acts similarly. The reference field can be integrated in simple fashion into the carrier stage, for example the X-Y displacement stage, that carries the wafer to be examined, and is thus easily accessible for an evaluation. The reference field can furthermore be provided on a special wafer. A reference field can likewise be provided on the particular wafer being produced.

In a first step, the setpoints are then determined by positioning the reference field in such a way that it can be illuminated with the illumination device. Illumination of the reference field is accomplished under defined conditions, in particular at a defined brightness and frequency. The radiation reflected from the reference field is acquired by a suitable image acquisition device as a bright- or dark-field image. Data that are representative of that defined adjustment of the illumination can thus be determined. In particular, the brightness or color balance of the previously adjusted illumination device can be obtained. These data are stored so that they are available again at a later point in time as well, by being read out of the memory.

For example, in order to determine the setpoints, once a macroscan has been programmed, the wafer is cleared, i.e. removed from the carrier stage. With the illumination adjusted identically, in particular with the frequency and brightness of the illumination device adjusted identically, a reference field is then positioned so that it is illuminated by that illumination apparatus that has now been adjusted in defined fashion. The reference field thus illuminated can therefore be measured, and the data representative of that illumination can be stored.

Those data can be read out again for the examination of subsequent wafers, so that the illumination device can be readjusted or corrections can be made to its illumination system. The reference field can thus be measured before the macroscan begins. The stored illumination setpoints can be read out and compared with the currently determined values. If this comparison yields discrepancies that are not acceptable in the specific case, for example because they exceed a predetermined magnitude, an adaptation of the illumination device can be performed. For adaptation, the illumination can then be modified until the differences between the current illumination value and the illumination setpoint are eliminated or reduced to an acceptable level. The stored illumination setpoints can be read out, and the reference fields evaluated, before each scan, at regular intervals (e.g. every few minutes, hours, or days), or after specific events, for example a replacement of the illumination system or the image acquisition device. Advantageously, this test interval can be set by the user without restriction.

The new illumination setpoints redetermined in this fashion can be stored instead of the original ones or in addition to them, and used for future adjustments.

It is also advantageous if the new illumination setpoints are compared with the old ones, and if additionally a comparison is performed with the control range still available for the illumination device. This makes it possible to ascertain whether the control range is still sufficient, or whether the illumination device will soon need maintenance. If the latter determination is made, a warning can be outputted to the user regarding the maintenance that will soon need to be performed.

BRIEF DESCRIPTION OF THE DRAWINGS

Further advantages and advantageous embodiments of the invention are the subject matter of the Figures below and their descriptions. In the individual Figures.

DETAILED DESCRIPTION OF THE INVENTION

Figure 1:
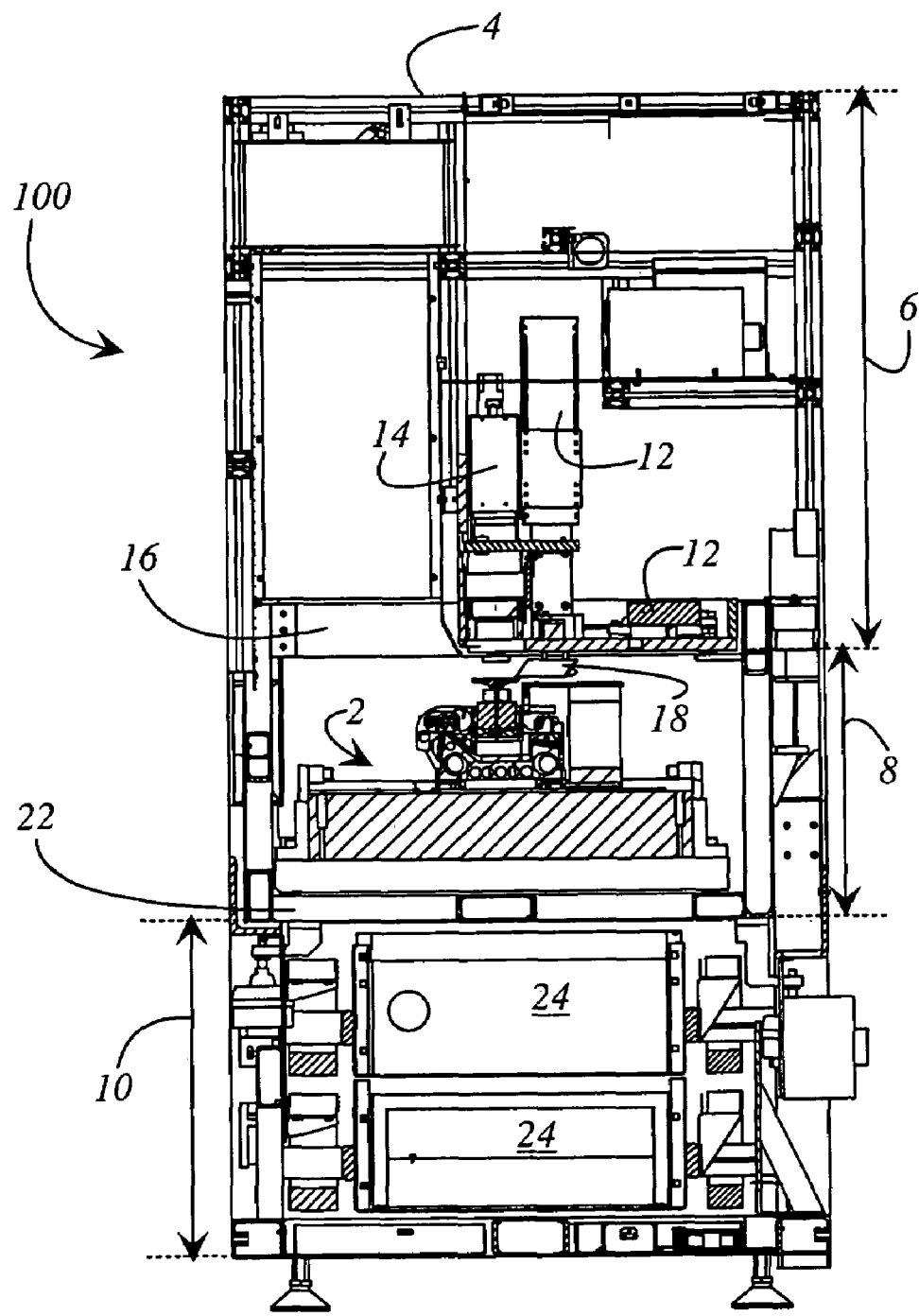
FIG. 1 schematically depicts the configuration of the overall system for the inspection of wafers and the detection of macrodefects.

FIG. 1 depicts an overall system 100 for the inspection of a wafer 26. System 100 is enclosed by a housing 4 and is subdivided into a first segment 6, a second segment 8, and a third segment 10. Housing 4 is closed off on all external surfaces by walls (not depicted), so that specific climatic or clean-room conditions are present in the interior of housing 4. Housed in first segment 6 of housing 4 are substantially several illumination devices 12 and at least one image acquisition device 14. Image acquisition device 14 is usually a CCD camera. First segment 6 is separated from second segment 8 by a mounting plate 16. The light of illumination devices 12 is directed via optical means 18 through mounting plate 16 onto the surface of the wafer to be inspected. Stage 2, which is movable in the X direction and Y direction, is provided in second segment 8. Stage 2 is mounted on a separating plate 22 that separates second and third segments 8 and 10 from one another. Third segment 10 encompasses several control units 20 or computers that are responsible for controlling, monitoring, and regulating system 100 and the individual components of system 100. In addition, data can likewise be acquired and evaluated therewith.

Figure 2:
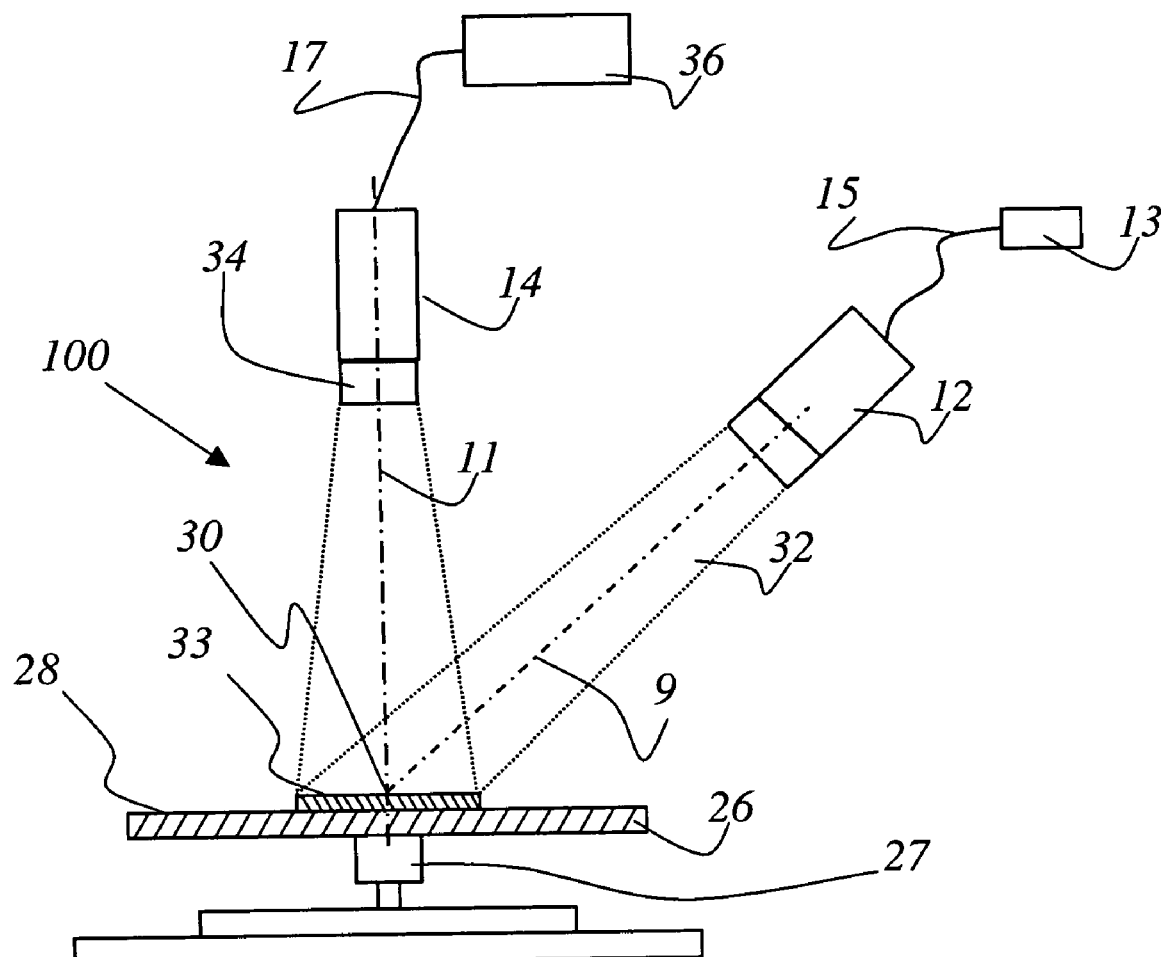
FIG. 2 schematically depicts a cross section through the apparatus according to the present invention.

FIG. 2 schematically shows wafer inspection apparatus 100 according to the present invention in cross section. It encompasses an illumination device 12 that defines an illumination axis 9 which intersects surface 28 of wafer 26 at incidence point 30. A camera serves as image acquisition device 14. Wafer 26 is carried by a wafer receiving device 27 that holds wafer 26 in stationary or also rotatable fashion. Wafer 26 is aspirated onto wafer receiving device 27 by vacuum. An illuminating light beam 32 proceeds from illuminating device 12 in such a way that illuminating light beams 32, incident in inclined fashion onto surface 28 of wafer 26 to be inspected, illuminate a corresponding region 33 that covers the entire surface 28 of wafer 26 or a subregion partial region thereof, for example individual dice.

Image acquisition device 14 is oriented perpendicularly onto surface 28 of wafer 26 and defines an imaging axis 11 that intersects surface 28 of wafer 26 at incidence point 30. An objective 34 is arranged at the front end of image acquisition device 14 so that illuminated region 33 is imaged into image acquisition device 14. Imaging axis 10 and illumination axis 9 span a plane that is orthogonal to surface 28 of wafer 26.

In FIG. 1, image acquisition device 14 and illumination device 12 are arranged in a dark-field configuration, so that what is imaged into image acquisition device 14 is not illuminating light reflected directly from surface 28 of wafer 26, but instead only scattered or diffracted light that derives from surface 28 of wafer 26 in illuminated region 33. As depicted in FIG. 1, illumination axis 9 is inclined with respect to surface 32 of wafer 6.

A light source can be provided directly in illumination device 12 or, as depicted in FIG. 1, can encompass an external light source 13 whose light is coupled via a light-guiding bundle 15 into the beam path. Light source 13 can be provided as a monochromatic or polychromatic light source. Suitable polychromatic light sources are, in particular, flash lamps, white-light LEDs, and the like. Preferably, however, light source 13 is driven in timed fashion, for example as a flash light that is triggered synchronously with image acquisition.

In very particularly preferred fashion, linear fiber illumination systems whose linearly emitted light is expanded with a cylindrical lens are used as illumination device 12.

Image acquisition device 14 can be connected via a data line 17 to an evaluation device 36 that evaluates or temporarily stores the acquired image data, for example for later image evaluation.

Before a wafer 26 is tested, firstly a "recipe" must be prepared, i.e. a procedure for testing the specific wafer 26 must be prepared and stored. For this programming step, the size of the dice present on the wafer is ascertained, this typically being an edge length between 20 and 50 mm. The position of the dice with respect to the wafer center point and the notch is also ascertained. The distribution of the dice on wafer 26 is additionally determined, so that it is known how close to the edge the dice are applied onto wafer 26. A determination is furthermore made as to which subregions of the dice are to be examined with which threshold. So-called color values of the wafer, which are used under the respective imaging conditions as reference values for the detection of defect-free wafers, are also acquired. Deviations from these reference values are detected as defects in the context of later measurements. These data ascertained in the programming process are stored as a so-called "recipe" for examining a group of identical wafers. The recipe is later loaded, automatically or manually by the user, for the examination of that exact wafer type.

Figure 3:
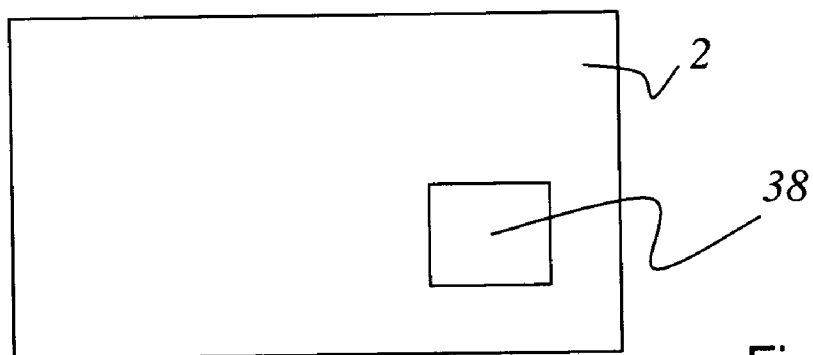
FIG. 3 is a schematic plan view of an X-Y stage.

According to the present invention, after programming and using the same illumination adjustments, in particular brightness and frequency, of illumination device 14, the brightness and color balance are sensed on a so-called reference field 38. As depicted schematically in plan view in FIG. 3, reference field 38 can be applied on X-Y stage 2 or integrated thereinto. Reference field 38 is preferably configured as a mirror surface having a defined reflectivity. It is thus possible, by measuring the reference field, to determine a reference value for the combination of illumination device 14 and image acquisition device 16 that corresponds to the present status, in particular to the present aging status, of the two components. The result of the measurement of reference field 38, i.e. the illumination setpoints, are stored in addition to the recipe, and can then be read out again in order to test or adjust illumination device 14. Adjustment of illumination device 12 can thus be accomplished in consideration of the stored illumination setpoints.

In principle, reference field 38 can also be applied on a sample wafer or on each wafer produced.

Figure 4:
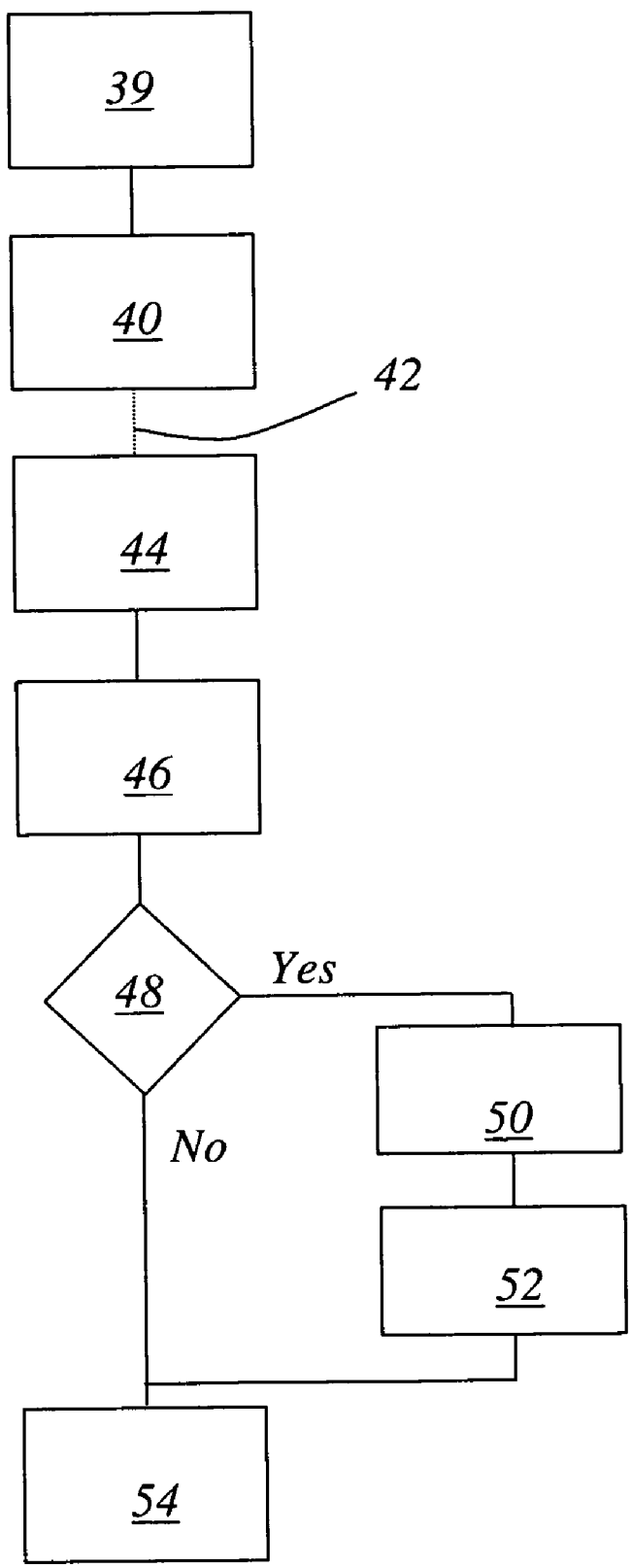
FIG. 4 schematically shows the flow chart of the method according to the present invention.

The flow chart in FIG. 4 schematically shows the sequence of the method according to the present invention. Firstly, in step 39 the macroscan necessary for the series of wafers 26 being produced is programmed as described above, the recipe for testing then being obtained therefrom. In step 40, with the illumination device identically adjusted, a reference field 38 (FIG. 3) is measured. The illumination setpoints thus determined are stored additionally or together with the recipe for the macroscan.

Before the macroscan is started in step 46, in step 44 the stored illumination setpoints are read out and illumination device 12 is adjusted using those values. Then, in step 46, the reference field is measured again using illumination device 12 adjusted in that fashion, and the result is compared with the stored data. If a discrepancy exceeding a defined threshold is ascertained in this comparison 48, the setpoints for illumination device 12 and/or the image acquisition device can then be rectified in step 50. The new setpoints can then be stored, separately or together with the recipe presently being used, in step 52. The macroscan can then be performed in step 54.

Dashed line 42 indicates that the stored illumination setpoints can be read out at different times as necessary. This is because system 100 for inspection of a wafer 26 is embodied to be differently configurable. The check of illumination device 12 initiated with step 48 can thus be performed at regularly succeeding time intervals, for example on the order of hours, days, or months. It is likewise possible to configure the system so that the check in step 48 is performed whenever a replacement of illumination device 12 and/or image acquisition device 14 in system 100 has taken place. The new setpoints for the new combination of illumination device 12 and image acquisition device 14 can be stored.

When the new setpoints are compared with the old setpoints, conclusions can also be drawn, from this difference, as to the aging status of illumination device 12 or image acquisition device 14. It is therefore also possible to infer from this difference that maintenance is imminent, or even that a component is about to fail. With this comparison, a warning signal can thus be outputted to the user. It is likewise possible to send an automatic request to a service technician if a connection, e.g. an online connection, is provided for that purpose.

What is claimed is:

1. A method for inspection of a wafer comprising the steps of:

emitting an illuminating light beam from an illumination device, wherein the light beam is incident onto a surface of the wafer, acquiring an image of the surface with an image acquisition device, and adjusting the illumination device, wherein the adjusting is accomplished in consideration of read-in stored illumination setpoints, wherein the setpoints for adjustment of the illumination device are determined by the fact that a reference field is illuminated by the illuminating light beam, and the image of the surface of the reference field is evaluated and an illumination setpoint is stored.

2. The method for inspection of a wafer as defined in claim 1, wherein a brightness value and/or an activation value is determined and stored as the illumination setpoint.

3. The method for inspection of a wafer as defined in claim 1, wherein the reference field is provided on a wafer support stage.

4. The method for inspection of a wafer as defined in claim 1, wherein the reference field is provided on a reference wafer or on the wafer itself that is to be examined.

5. The method for inspection of a wafer as defined in claim 1, wherein the setpoints are determined by the fact that once a macroscan has been programmed, the wafer is removed and the reference field is measured using the same illumination adjustment.

6. The method for inspection of a wafer as defined in claim 1, wherein the illumination setpoints are stored as reference values additionally.

7. The method for inspection of a wafer as defined in claim 1, wherein before inspection of the wafer begins, the reference field is re-measured, the value thus determined is compared with the illumination setpoint, and the adjustment of the illumination device is modified as applicable.

8. The method for inspection of a wafer as defined in claim 7, wherein an illumination setpoint update is stored.

9. The method for inspection of a wafer as defined in claim 7, wherein the reference field is measured before inspection of each wafer begins.

10. The method for inspection of a wafer as defined in claim 7, wherein the reference field is measured at regular time intervals before inspection of a wafer begins.

11. The method for inspection of a wafer as defined in claim 7, wherein the reference field is measured after each replacement of the illumination device and/or of the image acquisition device, before inspection of a wafer begins.

12. The method for inspection of a wafer as defined in claim 7, wherein in the event of a discrepancy between the illumination setpoint resulting from the re-measured reference field and the stored illumination setpoint, a warning signal is outputted.

13. The method for inspection of a wafer as defined in claim 12, wherein the warning signal is outputted when the difference between the stored illumination setpoint and the illumination setpoint resulting from the re-measured reference field exceeds a predetermined limit.

14. The method for inspection of a wafer as defined in claim 1, wherein adjusting the illumination device comprises adjustment of the brightness or frequency.

15. The method for inspection of a wafer as defined in claim 2, wherein the brightness value and/or activation value is a voltage value for the illumination device.

16. The method for inspection of a wafer as defined in claim 3, wherein the wafer support stage is an X-Y displacement stage.

17. The method for inspection of a wafer as defined in claim 6, wherein the illumination setpoints are stored with a determined recipe for a macroscan.

18. The method for inspection of a wafer as defined in claim 12, wherein the warning signal is a warning signal that maintenance is imminent.

* * * * *